United States Patent [19]

Farquhar

[11] Patent Number: 4,816,570
[45] Date of Patent: Mar. 28, 1989

[54] BIOLOGICALLY REVERSIBLE PHOSPHATE AND PHOSPHONATE PROTECTIVE GROUPS

[75] Inventor: David Farquhar, Houston, Tex.

[73] Assignee: The Board of Regents of the University of Texas System, Austin, Tex.

[21] Appl. No.: 848,741

[22] Filed: Apr. 4, 1986

Related U.S. Application Data

[63] Continuation-in-part of Ser. No. 445,653, Nov. 30, 1982, abandoned.

[51] Int. Cl.$^4$ .................. C07H 19/10; C07H 19/20
[52] U.S. Cl. .................................. 536/27; 536/284; 536/29
[58] Field of Search ............... 536/27, 28, 29; 514/51

[56] References Cited

U.S. PATENT DOCUMENTS

| | | | |
|---|---|---|---|
| 3,188,309 | 6/1965 | Mukaiyama | 260/211.5 |
| 3,284,440 | 11/1966 | Patchett | 260/211.5 |
| 3,463,772 | 8/1969 | Nagyvary | 260/211.5 |
| 3,701,772 | 10/1982 | Tamura | 260/211.5 R |
| 3,847,898 | 11/1974 | Kelly | 260/211.5 R |
| 4,048,307 | 9/1977 | Yokota | 424/180 |
| 4,056,673 | 11/1977 | Heimer | 536/27 |
| 4,093,714 | 6/1978 | Tolman | 424/180 |
| 4,096,324 | 6/1978 | Kelly | 536/23 |
| 4,239,905 | 12/1980 | Kodama | 536/29 |

OTHER PUBLICATIONS

D. Farquhar et al, *Proceedings of the 13th International Cancer Congress*. Abstract 1789 (1982).
Leong, Latent Antitumor Nucleotides, 1980.
Srivastva, Organic Chemistry, presented before J.C.S. 1982, Kansas City.
Srivastva et al, Biomedical Mass Spectometry 1982.
Farquhar et al, J. of Phar. Sciences, 72, No. 3 (1983).
De Clercq, Meth. and Find. Expl. Clin. Pharmacol, 2(5), 253–267 (1980).
*Indexus Chemicus*, 18 No. 4, 54614 (Aug. 2, 1965).

M. MacCoss et al, 46 *4th International Round Table* (Antwerp, 4–6 Feb. 1981).
D. C. Remy et al, 27 Journal of Org. Chem. 27,2491–2500 (1962).
D. A. Leong, Latent Antitumor Nucleotides, 1980.
D. Farquhar, Notice of Research Report, Submitted to American Cancer Society , Inc. (Grant Application) (3–6–79).
D. N. Srivastva, Organic Chemistry, Biologically Reversible Phosphate-Protective Groups (Abstract) 1982 Presented before American Chem. Soc., Kansas City.
D. N. Srivastva et al, Biomedical Mass Spectrometry (1982) Mass Spectral Characterization of Acyloxymethyl Phosphates.
K. C. Liebman et al, 216 *Journal of Biol. Chem.* 823–830, (1955).
P. M. Roll et al, 220 *Journal of Biol. Chem.* 439–454 (1955).
E. K. Euranto et al, 20 *Acta Chem. Scan.* 1273–1280 (1966).
J. P. H. Verheyden et al, 35 *J. Org. Chem.* 2319 (1970).
P. P. Saunders et al, 30 *Biochem. Pharm.* 2374 (1981).
D. G. I. Kingston et al. 75 *Chem. Reviews* 693 (1975).
C. C. Coffin, 5 Canad. Journal Research 636 (1931).
J. A. Montgomery et al, 26 *Journal of Medic. Chem.* 1929 (1961).

(List continued on next page.)

Primary Examiner—Johnnie R. Brown
Assistant Examiner—Jenny Tou
Attorney, Agent, or Firm—Arnold, White & Durkee

[57] ABSTRACT

Protective groups are provided which are suitable for masking phosphates and phosphonates. The protected compositions can be introduced in a biological system and then demasked under certain biological conditions. This method permits phosphates and phosphonates which would themselves degrade in the biological system and therefore be ineffective to be introduced in a protected form and late released under the proper conditions.

6 Claims, 1 Drawing Sheet

OTHER PUBLICATIONS

J. A. Montgomery et al. 22 *Cancer Research* 504 (1962).
H. J. Thomas et al, 11 *Journal Medic Chem.* 44 (1968).
J. Nagyvary, 55 Biochem. and *Biophys. Research Commun.* 1072 (1973).
R. N. Gohil, 1 *Nucleic Acids Res.* 1691 (1974).
E. J. Norman, 17 Journal Medic. Chem. 473 (1974).
W. V. Daehne, 13 *Journal Medic. Chem.* 607 (1970).
W. J. Wheeler, 22 *Journal Medic. Chem.* 657 (1979).
D. Farquhar, et al, *Journal of Pharmaceutical Sciences*, vol. 72, No. 3 (1983).
D. Farquhar, *International Congress of Chemistry*, Hawaii (Dec. 1984).
Srivastva et al, *Bioorganic Chemistry* 12, 118–129 (1984).

BIOLOGICALLY REVERSIBLE PHOSPHATE AND PHOSPHONATE PROTECTIVE GROUPS

This patent application is a continuation-in-part of Ser. No. 445,653, filed on Nov. 30, 1982, now abandoned.

BACKGROUND OF THE INVENTION

This invention relates to the use of biologically reversible protective groups in medicinal chemistry. More particularly, it relates to providing ionic phosphate and phosphonate compounds intracellularly in biological systems through the use of biologically reversible protective groups.

Bioreversible protective groups and their uses are well-known in medicinal chemistry. Some compounds that are potentially useful in biological systems cannot be directly provided in those systems, because they will be rapidly decomposed or are otherwise incompatible with that biological environment in a way that renders them ineffective. However, when this type of compound is derivatized with protective groups, the composite product usually has different physical and chemical properties that the parent. These modified properties can make the product suitable for introduction into certain biological environments that its parent is not. If the protective groups are later removed under biological conditions, the parent compound is left to perform its useful function.

This general method has a number of applications. For example, if the parent is unstable under the relevant biological conditions, it can be derivatized with protective groups which will create a more stable product. The protective groups can be selected so that they will be removed under predetermined biological conditions that exist at the site in the system where the parent is needed.

One area where this concept has apparently not yet been applied with satisfactory results is in the manipulation of phosphate and phosphonate compounds. These compounds, particularly phosphomonoesters and phosphodiesters, play a key role in cellular metabolism. They are involved in almost every metabolic sequence, including the synthesis of carbohydrates, lipids, amino acids, proteins, nucleotides and nucleic acids. One logical way to regulate these metabolic processes is to inhibit intracellular phosphate metabolizing enzymes by using structurally analogous phosphates. These phosphoesters have very substantial therapeutic potential, but thus far they have not been practically useful, because they usually cannot penetrate cell membranes.

There are two reasons for this penetration problem. First, these phosphoesters are negatively charged at physiologic pH and are highly hydrophilic. Consequently, they are chemically incompatible with lipid membranes. Second, most of these compounds are rapidly degraded by enzymes in the blood and on cell surfaces.

As an example, most purine and pyrimidine antimetabolites used in the treatment of cancer require intracellular conversion to the corresponding 5'-mono-, di-, or tri-phosphates in order to exert cytotoxicity. In experimental tumors, resistance to these agents frequently correlates with the deletion or decreased activity of enzymes that convert the administered drugs to the 5'-mononucleotides.

These problems have been recognized since about 1955. A number of attempts have been made to overcome them by using protective groups to change the phosphates into neutral, lipophilic derivatives which could resist the blood and cell surface enzymes. These derivatives would theoretically enter the target cells and then be demasked. This has apparently never been satisfactorily achieved in practice. Prior art masked phosphates have basically proved to be biologically inert. This is believed to be attributable to their failure to demask under biological conditions.

Thus, there remains a need for means to provide useful phosphates and phosphonates intracellularly. For this goal to be achieved through the use of protective groups, the masked phosphate must not be degraded by blood or cell surface enzymes and the protective groups must be removed under the biological conditions that exist in the target cells.

SUMMARY OF THE INVENTION

Bioreversibly protected phosphate or phosphonate compositions in accordance with the present invention use either of two types of protective groups that can be cleared by enzymes known to exist in the body. ("Bioreversibly protected phosphate or phosphonate composition" is used in this specification and the appended claims to refer to a parent phosphate or phosphonte which has been derivatized with a protective group of groups.) When a phosphate is derivatized with the first type of protective group, the protected composition has the formula:

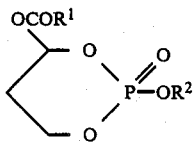

When a phosphonate is derivatized with the first type of protective group, the protected composition has the formula:

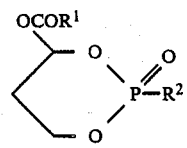

$R^1$ can be hydrogen; alkyl, alkaryl, or aryl hydrocarbon, or an organic derivative thereof (e.g., nitroalkyl, haloalkyl, aminoalkyl, carboxyalkyl, nitroaryl, haloaryl, aminoaryl, carboxyaryl, etc); or amine. $R^1$ is preferably an alkyl, alkaryl, or aryl hydrocarbon having from 1–10 carbon atoms; or an amine having the formula $NR^4R^5$, where $R^4$ and $R^5$ are independently hydrogen or an alkyl hydrocarbon having from 1–10 carbon atoms. $R^1$ is most preferably an alkyl, alkaryl, or aryl hydrocarbon having from 1–6 carbon atoms; or $N(CH_3)_2$.

$R^2$, part of the parent phosphate or phosphonate, can be any organic or inorganic residue, such as a sugar, nucleoside, lipid, amino acid or polypeptide. $R^2$ is preferably hydrogen; an alkyl, alkaryl, aryl or alkoxycarbonyl hydrocarbon; or a nucleoside such as a 2'-deoxynucleoside.

When a phosphate is derivatized with the second type or protective group, the protected composition has the formula:

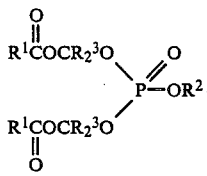

When a phosphonate is derivatized with the second type of protective group, the protected composition has the formual:

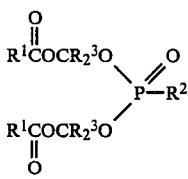

$R^1$ can be hydrogen; alkyl, alkaryl, or aryl hydrocarbon, or an organic derivative thereof; or amine. $R^1$ is preferably an alkyl, alkaryl, or aryl hydrocarbon having from 1-10 carbon atoms; or an amine having the formula $NR^4R^5$, where $R^4$ and $R^5$ are independently hydrogen or an alkyl hydrocarbon having from 1-10 carbon atoms. $R^1$ is most preferably an alkyl, alkaryl, or aryl hydrocarbon having from 1-6 carbon atoms; or $N(CH_3)_2$.

$R^3$ is hydrogen or an alkyl hydrocarbon, preferably hydrogen or a methyl group.

$R^2$, part of the parent phosphate or phosphonate, again can be any organic or inorganic residue, such as a sugar, nucleoside, lipid, amino acid or polypeptide. $R^2$ is preferably hydrogen; alkyl, alkaryl, aryl, or alkoxycarbonyl hydrocarbon; or a nucleoside, such as a 2'-deoxynucleoside.

$R^2$ substituents that are particularly useful for a number of applications with either type of protective group include nucleosid-5'-yl groups, such as 2'-deoxynucleosid-5'-yl groups, and analogs thereof.

Both types of protected compositions are resistant to the blood and cell surface enzymes that degrade the parent phosphates. Furthermore, they both demask under biological conditions, so that at least some of the parent phosphates or phosphonates will be able to perform their desired intracellular functions.

The demasking mechanism is believed to be slightly different for the two types of protected compositions. For the first time, it appears to begin with the degradation of the protected phosphate or phosphonate to an unstable intermediate by carboxylate esterase. Cell-penetration may occur before or after this step. However, once the parent compound is completely demasked, it is once again unable to penetrate cell membranes. The unstable intermediate spontaneously ring opens to form its aldehydo tautomer. Next, the tautomer spontaneously eliminates acrolein, leaving the parent phosphate or phosphonate.

The demasking mechanism for the second type also appears to begin with degradation by carboxylate esterase, this time forming an unstable first intermediate. The first intermediate spontaneously eliminates an aldehyde or ketone to create a second intermediate, which is in turn degraded by carboxylate esterase to form an unstable third intermediate. The third intermediate spontaneously eliminates another aldehyde or ketone, leaving the parent phosphate or phosphonate. As with the first type, cell-penetration can be before or after degradation begins, but must be before the phosphate or phosphonate is completely demasked.

With either type of protective group, some of the protected compositions may break down outside cell membranes. However, at least some of the phosphates or phosphonates should be released within the target cells where they can be used for a variety of purposes.

One species of the second type of protective group, acyloxymethyl radicals, has been used in the past to mask carboxylic acids. However, neither they nor the first type have apparently ever been used in conjunction with phosphates or phosphonates.

The $R^1$ and $R^3$ substituents on these two types of protective groups can be modified to give the masked composition almost any desired physical or chemical property. By thus controlling the properties of the protected composition, variables such as location and rate of demasking can be controlled. This method has potential applications in modulating biochemical pathways, abrogating metabolic deficiencies, circumventing resistance to anticancer drugs and developing new anticancer, antiviral, and antiparasitic drugs.

BRIEF DESCRIPTION OF THE DRAWINGS

In accordance with the present invention.

DETAILED DESCRIPTION OF SPECIFIC EMBODIMENTS

The present invention relates to protective groups that can be used to mask phosphates or phosphonates. The protected composition demasks under biological conditions, thus leaving the parent phosphate or phosphonate available for reaction. This method has potential medical applications with any phosphate or phosphonate which has a therapeutic effect. (As used in this application and the appended claims, "therapeutic effect" means the diagnosis, cure, mitigation, treatment, or prevention of disease in man or other animals, or an effect on the structure or any function of the body of man or other animals.)

Figure 1:
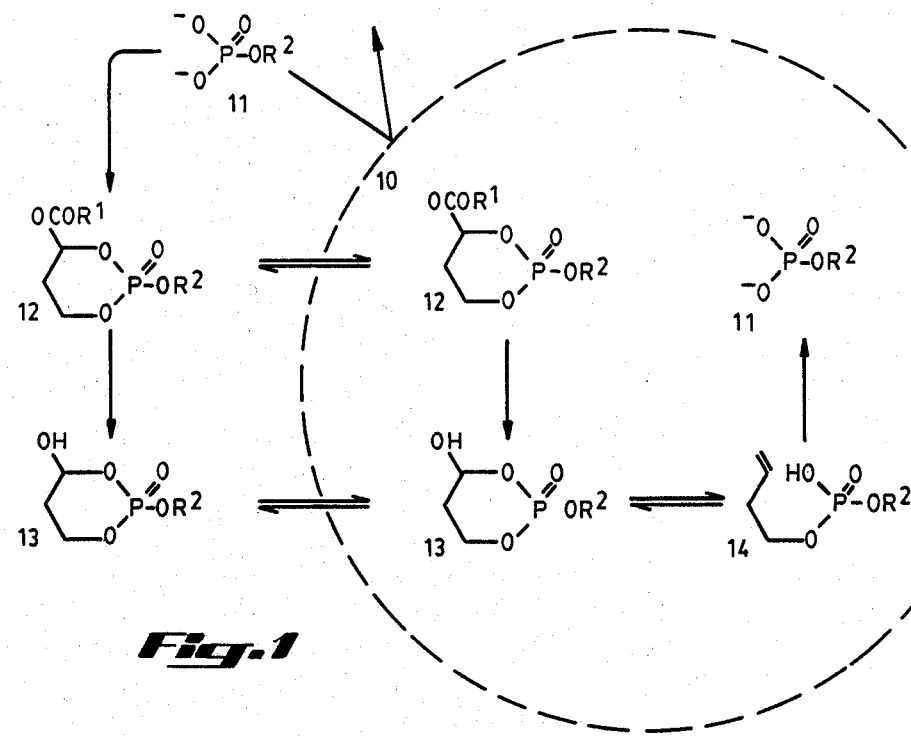
FIG. 1 shows the demasking mechanism believed to occur for the first type of phosphate protective group.

One type of protective group and a method for its use is shown in FIG. 1. A parent phosphate 11 is derivatized with the first type of protective group to form a bioreversibly protected composition 12. The $R^1$ and $R^2$ substituents on this composition can be as previously described.

The protected composition 12 is introduced into a biological system. While the parent phosphate 11 could not penetrate cell membranes 10, the protected composition 12 can. Carboxylate esterase degrades the protected composition 12, either before or after cell penetration, and produces an unstable intermediate 12. The intermediate 12 spontaneously ring opens to form its aldehydo tautometer 14. The tautometer 14 spontaneously eliminates acrolein to give the parent logic phosphate 11.

The mechanism would be the same for a protected phosphonate.

Figure 2:
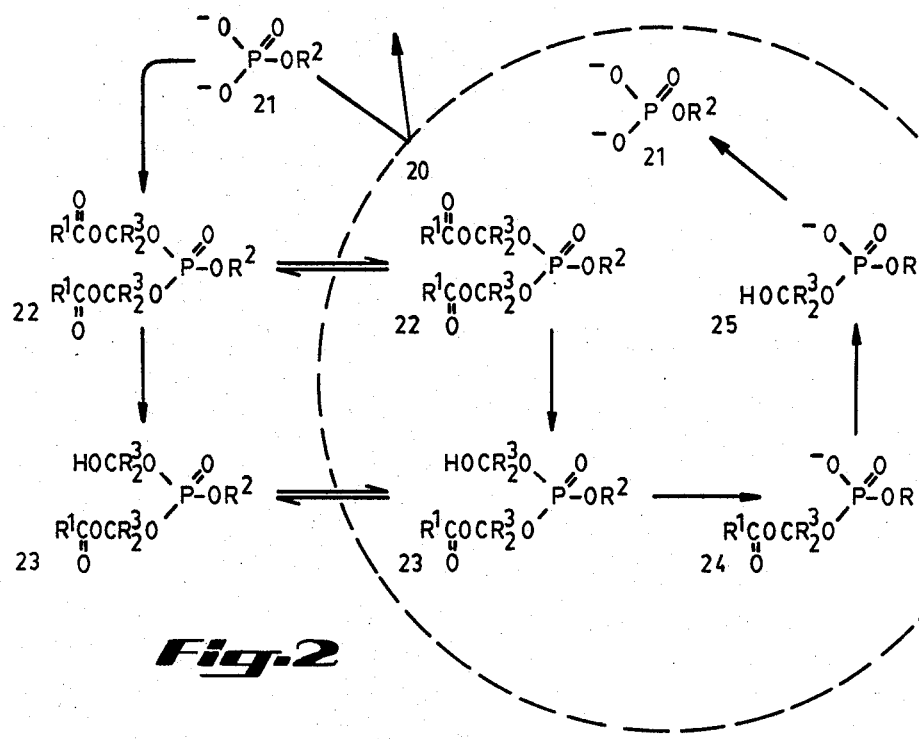
FIG. 2 shows the demasking mechanism believed to occur for the second type of phosphate protective group.

A second type of protective group and its use are shown in FIG. 2. A parent phosphate 21 is derivatized with the second type of protective group to form a protected composition 22. $R^1$, $R^2$, and $R^3$ can be as previously described. The protected composition 22 is capable of penetrating cell membranes 20, and can do so before or after degradation begins.

Carboxylate esterase degrades the protected composition 22 to an unstable first intermediate 23. The first intermediate 23 then spontaneously eliminates an aldehyde or ketone to create a second intermediate 24. Carboxylate esterase degrades the second intermediate 24 to given an unstable third intermediate 25. This substance spontaneously loses an aldehyde or ketone, leaving the parent phosphate 21.

The mechanism would be the same for a protected phosphonate.

Several tests have been peformed with both types of protected compositions. These protected compositions have proved to be biologically active, unlike the prior art masked phosphates. The stabilities of these protected compositions were determined in aqueous buffered solutions having pH ranging from 1 to 10, and also under selected biological conditions. Except for the acetoxymethyl derivatives of the second type, these phosphoesters were relatively stable in a neutral environment. They reverted to their parent compounds in acidic or basic media.

The derivatization reaction for both types of protected compositions can be carried out in a number of ways. Several possibilities are described below. Example 1 concerns the first type of protected composition and the remainder of the examples concern the second type.

EXAMPLE 1

A solution of acrolein (6.72 g, 8.01 ml) in anhydrous chloroform (50 ml) was cooled to 5° C. in an ice bath. Dry hydrogen bromide gas was then introduced with stirring until the solution was saturated. Pivaloyl bromide (28.6 g) was added, followed by 0.2 g of zinc chloride, and the reaction mixture was stirred at room temperature for 5 days. The crude reaction product was directly fractionated to yield 16.4 g of 1,3-dibromo-1-pivaloyloxypropane. The boiling point of this product was 85° C. at 1.5 mm Hg.

Anhydrous sodium iodide (1.24 g, 0.00082 mole) was dissolved in dry acetone (25 ml), and the solution was treated dropwise with stirring under a dry nitrogen atmosphere with a solution of the 1,3-dibromo-1-pivaloyloxypropane (1.00 g, 0.0033 mole) in acetone (3.0 ml). After stirring at ambient temperature for 3 hours, the reaction mixture was poured into dry hexane (150 ml).

Insoluble salts were removed by filtration, under nitrogen, through a bed of diatomaceous earth. The yellow filtrate was concentrated on a rotary evaporator at less than 30° C. The remaining oil was taken up in dry hexane (30 ml) and again filtered to remove some insoluble residue. The solution was concentrated as described above to give 1.40 g of a light yellow oil.

On attempted distillation this product underwent extensive decomposition. Since the IR, NMR and MS of the compound were consistent with the anticipated structure, and since the compound gave satisfactory elemental analytical data, it was used in subsequent reactions without further purification.

Next a solution of the 1,3 diiodo-1-pivaloyloxypropane (1.4 g) in dry ethylene glycol dimethyl ether (10 ml) was added with stirring under a dry nitrogen atmosphere to a solution of bis(tetrabutylammonium)phenyl phosphate (2.17 g, 0.0033 mole) in dry ethylene glycol dimethyl ether (200 ml). (Thus, $R^2$ was $C_6H_5$.) The reaction mixture was refluxed for 2 hours and then cooled to room temperature and filtered through a sintered glass funnel.

After removal of solvent on a rotary evaporator at less then 80° C., the residual oil was preadsorbed on dry-column silica gel (20 g) which was then transferred to a 30"×1" column of the same adsorbent. The column was developed with ethyl acetate-hexane (80/20, v/v). Product bands were located by inspection under UV light (254 nm). The products were eluted from the silica gel with chloroform and further purified by chromatography on two thick-layer silica plates (20 cm×20 cm×2 mm). The products, which were obtained as viscous oils, were shown by MS and NMR to be stereoisomers (arising from the presence of two chiral centers in the molecule at positions 2 and 4). The total yield for the four isomers was 210 mg.

Although the product was stable in organic solvents or aqueous buffers, it was quantitatively converted to phenyl phosphate when treated with strong acids or bases. Similarly, the product reverted to phenyl phosphate when incubated at 37° C. for 30 minutes with mouse plasma.

This synthesis can be summarized as follows:

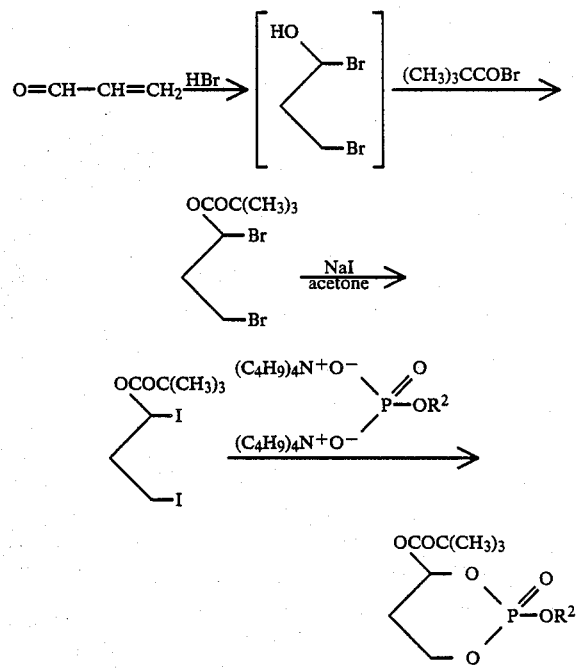

This procedure was later repeated using bis(tetrabutylammonium)benzyl phosphate, i.e., with the $R^2$ substituent being $C_6H_5CH_2$.

EXAMPLE 2

A disilver phosphate was obtained from the corresponding disodium salt by reaction with silver nitrate in water. The disilver phosphate was reacted with a 2.5 molar excess of an iodomethyl ester in anhydrous benzene at room temperature for about 5 hours. The product was a bis(acyloxymethyl)phosphate. Several runs of this reaction were performed.

This synthesis can be summarized as follows:

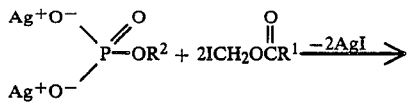

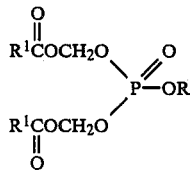

In this run, the $R^2$ substituent of the parent phosphate was $C_6H_5$ and the $R^1$ substituent of the protective group was $CH_3$. The product of this reaction was bis(acetoxymethyl)phenyl phosphate and the yield was 5%.

The protected product was stable in neutral aprotic solvents such as benzene, diethyl ether and ethyl acetate. However, in protonic solvents such as ethanol, water or 0.05M potassium phosphate buffer (pH 7.4), it was slowly converted to mono(acetoxymethyl)phenyl phosphate. The half-life was greater than 4 hours.

These solutions were analyzed by (HPLC) high performance liquid chromatography (Waters model ALC 204). The disappearance of the bis(acyloxymethyl)phosphate was monitored by reversed-phase chromatography on a column of μ Bondapak-$C_{18}$ (30 cm×4 mm i.d., 10 μm; Waters Assoc., Milford, Mass.) using solutions of 0.01M potassium phosphate buffer (pH 7.0) with methanol as the mobile phase (typically 25-50% alcohol).

The mechanism for this change is probably as shown below.

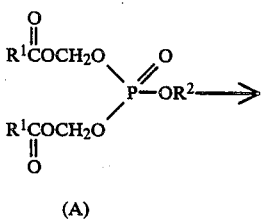

(A)

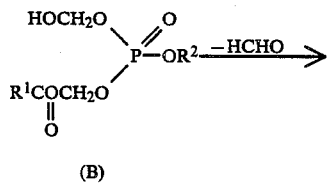

(B)

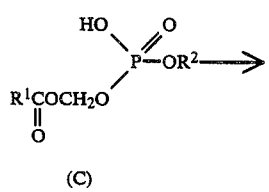

(C)

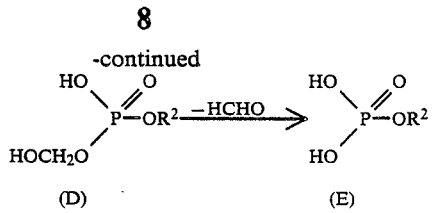

(D)       (E)

The bis(acetoxymethyl)phosphate A is solvolyzed to form an intermediate B, which spontaneously eliminates formaldehyde. A mono(acetoxymethyl)phosphate C results, and is further demasked to a next intermediate D and the parent phosphate E by repetition of the same steps. A labile intermediate was detected in some solutions by HPLC, but was not characterized.

The formation of intermediate B and mono(acetoxymethyl)phosphate C was monitored by ion-pair chromatography on μ Bondapak-C using the same buffer system as described above, except that tetrabutylammonium hydroxide was added to a concentration $2 \times 10^{-3}$M, or by anion-exchange chromatography on a column of partisil SAX (25 cm×4.6 mm i.d., 10 m; Whatman) using a linear gradient of 0.01-0.1M potassium phosphate buffer (pH 6.5) as an eluent. The flow rates for these analyses and the ones described above ranged from 1.0 to 2.0 ml/min. The column effluents were monitored at 254 nm with a Schoeffel model 450 UV detector, and the concentrations were determined by comparison of the peak areas with those of reference standards.

When the bis(acetoxymethyl)phenyl phosphate was incubated at a concentration of 65 micrograms per milliliter at 37° C. in 0.05M potassium phosphate buffer (pH 7.4) with either hog liver carboxylate esterase (obtained from Sigma Chemicals, St. Louis, Mo.) (E.C. No. 3.1.1.1., 8 milligrams portein per milliliter) or mouse plasma (50% by volume) it was rapidly degraded, first to the mono(acetoxymethyl) analog, and then to the parent phenyl phosphate. The half-life was less than 15 minutes. (At appropriate intervals, aliquots (100 ul) of the incubation mixtures were diluted with 3 volumes of methanol and then agitated for 1 minute on a Vortex shaker. The precipitated protein was separated by centrifugation at 10,000×g for 5 minutes, and the supernatants were analyzed by HPLC as described above.)

EXAMPLE 3

In this case iodomethyl pivaloate was used (i.e., $R^1$ was $C(CH_3)_3$). Preparation was otherwise the same as in Example 2. The product, bis(pivaloyloxymethyl)phenyl phosphate, was produced with 54% yield.

This phosphotriester was much more resistant to both chemical and enzymatic hydrolysis than the protected composition of Example 1. It was stable in protonic solvents and had a half-life of about 5 hours when incubated with mouse plasma under the same conditions as in Example 2. This demonstrates that the acyl substituent has a substantial effect on the rate of hydrolysis.

EXAMPLE 4

Disilverbenzyl phosphate was reacted with iodomethyl pivaloate. The product was bis(pivaloyloxymethyl)benzyl phosphate. Catalytic hydrogenolysis of this product over 5% Pd-C in cyclohexane gave the corresponding monobasic acid. This acid was isolated in its cyclohexyl ammonium salt form.

Successive ion exchange of the salt on Dowex 50 $Na^+$ and Dowex 50 $Ag^+$ produced silver bis(- pivaloyloxymethyl)phosphate. This compound is very useful in synthesizing other bis(acyloxymethyl)phosphoesters. For example, when reacted with benzyl bromide or methyl iodide in benzene at room temperature for about 5 hours, the corresponding benzyl and methyl phosphotriesters are produced in nearly quantitative yield.

The synthesis of this example can be summarized as follows:

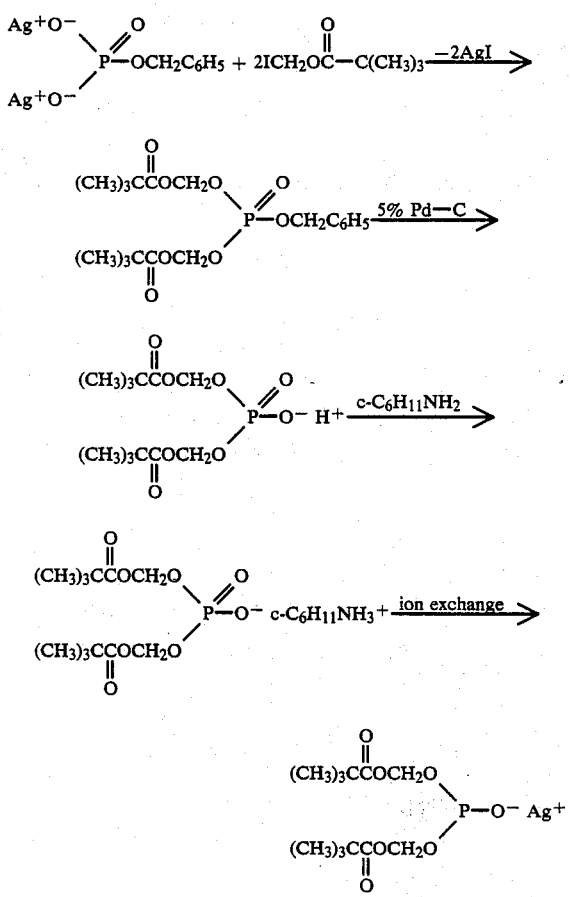

EXAMPLE 5

The silver diester product of Example 4 was reacted with 5'-deoxy-5'-iodo-3-O-acetylthymidine, as shown below.

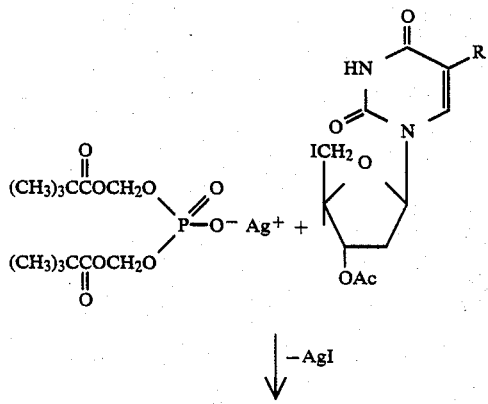

-continued

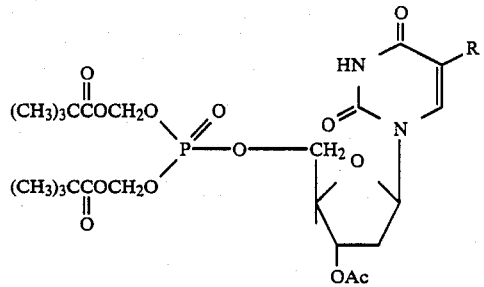

The R substituent shown was a methyl group.

The reaction was carried out under reflux for about 5 hours. Bis(pivaloyloxymethyl) 3'-O-acethythymidine-5'-phosphate was produced in 39% yield.

EXAMPLE 6

Example 5 was repeated with the R substituent changed to fluorine (i.e., 2',5-dideoxy-5'-iodo-3'-O-acetyl-5-fluorouridine). There was a 15% yield of this product. This composition prevented the growth of Chinese hamster ovary cells in culture at a concentration of $5.0 \times 10^{-6}$M [5-fluoro-2'-deoxyuridine (5-FUdR) control, $1.0 \times 10^{-6}$M].

EXAMPLE 7

Several bis(acyloxymethyl)esters of 5-fluoro-2'-deoxyuridine-5" phosphate (5-FdUMP) were prepared through condensation of 5-FUdR or 3'-O-acetyl-5-FUdR with bis(acyloxymethyl)phosphates. One in particular, 5-FUdR-(3'-OCOCH$_3$)-5'-O-[P(O)(OCH$_2$OCOC(CH$_3$)$_3$)$_2$], was incubated at 3° C. with mouse plasma and hog liver carboxylate esterase. The acyloxymethyl groups and the 3'-acetyl group were successively cleaved to give 5-FdUMP. When the bis(acyloxymethyl)ester was tested, it prevented the growth of Chinese hamster ovary cells in culture at a concentration of $1 \times 10^{-6}$M. It also proved active against P388 leukemia which is resistant to 5-fluorouracil.

EXAMPLE 8

Using generally the same synthetic methods described in the previous examples, the following compounds were synthesized. Table 1 lists phosphates and Table 2 lists phosphonates.

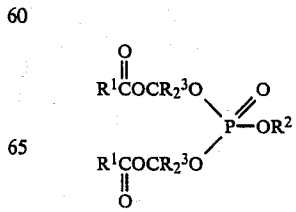

TABLE 1

| Compound | R¹ | R³ | R² |
|---|---|---|---|
| 1 | $CH_3$ | H | $C_6H_5$ |
| 2 | $C_2H_5$ | H | $C_6H_5$ |
| 3 | $(CH_3)_2CH$ | H | $C_6H_5$ |
| 4 | $(CH_3)_3C$ | H | $C_6H_5$ |
| 5 | $(CH_3)_3C$ | $CH_3$ | $C_6H_5$ |
| 6 | $C_4H_9$ | H | $C_6H_5$ |
| 7 | $C_6H_5$ | H | $C_6H_5$ |
| 8 | $(CH_3)_2N$ | H | $C_6H_5$ |
| 9 | $(CH_3)_3C$ | H | $CH_3$ |
| 10 | $CH_3$ | H | $C_6H_5NO_2$ |
| 11 | $(CH_3)_2CH$ | H | $C_6H_5NO_2$ |
| 12 | $(CH_3)_3C$ | H | $C_6H_5NO_2$ |
| 13 | $CH_3$ | H | $C_6H_5NH_2$ |
| 14 | $(CH_3)_2CH$ | H | $C_6H_5NH_2$ |
| 15 | $(CH_3)_3C$ | H | $C_6H_5NH_2$ |
| 16 | $CH_3$ | H | $CH_2OCOCH_3$ |
| 17 | $(CH_3)_2CH$ | H | $CH_2OCOCH(CH_3)_2$ |
| 18 | $(CH_3)_3C$ | H | $CH_2OCOC(CH_3)_3$ |
| 19 | $CH_3$ | H | $CH_2C_6H_5$ |
| 20 | $C_2H_5$ | H | $CH_2C_6H_5$ |
| 21 | $(CH_3)_2CH$ | H | $CH_2C_6H_5$ |
| 22 | $(CH_3)_3C$ | H | $CH_2C_6H_5$ |
| 23 | $(CH_3)_3C$ | $CH_3$ | $CH_2C_6H_5$ |
| 24 | $C_6H_5$ | H | $CH_2C_6H_5$ |
| 25 | $(CH_3)_2N$ | H | $CH_2C_6H_5$ |
| 26 | $CH_3$ | H | H |
| 27 | $C_2H_5$ | H | H |
| 28 | $(CH_3)_2CH$ | H | H |
| 29 | $(CH_3)_3C$ | H | H |
| 30 | $C_4H_9$ | H | H |
| 31 | $(CH_3)_3C$ | $CH_3$ | H |
| 32 | $C_6H_5$ | H | H |
| 33 | $(CH_3)_2N$ | H | H |
| 34 | $CH_3$ | H | 2'-deoxy-5-fluorouridin-5'-yl |
| 35 | $C_2H_5$ | H | 2'-deoxy-5-fluorouridin-5'-yl |
| 36 | $(CH_3)_2CH$ | H | 2'-deoxy-5-fluorouridin-5'-yl |
| 37 | $(CH_3)_3C$ | H | 2'-deoxy-5-fluorouridin-5'-yl |
| 38 | $C_4H_9$ | H | 2'-deoxy-5-fluorouridin-5'-yl |
| 39 | $C_6H_5$ | H | 2'-deoxy-5-fluorouridin-5'-yl |
| 40 | $(CH_3)_2N$ | H | 2'-deoxy-5-fluorouridin-5'-yl |
| 41 | $(CH_3)_3C$ | H | 2'-deoxy-3'-O—acetyl-5-fluoro uridin-5'-yl |
| 42 | $(CH_3)_3C$ | H | 2'-deoxyuridin-5'-yl |
| 43 | $(CH_3)_3C$ | H | 2'-deoxy-5-bromouridin-5'-yl |
| 44 | $(CH_3)_3C$ | H | 2'-deoxy-5-iodoouridin-5'-yl |
| 45 | $(CH_3)_3C$ | H | 2'-deoxy-5-(bromovinyl)-uridin-5'-yl |
| 46 | $(CH_3)_3C$ | H | 5'-fluorouridin-5'-yl |
| 47 | $(CH_3)_3C$ | H | thymidin-5'-yl |
| 48 | $(CH_3)_3C$ | H | 3'-O—acetylthymidin-5'-yl |

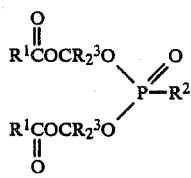

TABLE 2

| Compound | R¹ | R³ | R² |
|---|---|---|---|
| 1 | $CH_3$ | H | $C_6H_5$ |
| 2 | $C_2H_5$ | H | $C_6H_5$ |
| 3 | $(CH_3)_2CH$ | H | $C_6H_5$ |
| 4 | $(CH_3)_3C$ | H | $C_6H_5$ |
| 5 | $CH_3$ | H | $C_6H_5NO_2$ |
| 6 | $C_2H_5$ | H | $C_6H_5NO_2$ |
| 7 | $(CH_3)_2CH$ | H | $C_6H_5NO_2$ |
| 8 | $(CH_3)_3C$ | H | $C_6H_5NO_2$ |
| 9 | $CH_3$ | H | $C_6H_5NH_2$ |
| 10 | $C_2H_5$ | H | $C_6H_5NH_2$ |
| 11 | $(CH_3)_2CH$ | H | $C_6H_5NH_2$ |
| 12 | $(CH_3)_3C$ | H | $CH_2C_6H_4NO_2$ |
| 13 | $(CH_3)_3C$ | H | $CH_2C_6H_4NH_2$ |
| 14 | $(CH_3)_3C$ | H | $CH_2C_6H_4NHCH(CH_3)_2$ |

Testing of these compounds has confirmed that the protective groups are removed under the appropriate conditions. Some of the compounds have been tested for biological activity, and have shown positive results.

The preceding examples and description are intended to be illustrative, but not to limit the scope of the invention. Those skilled in the art will appreciate that the present invention has a number of potential applications and a variety of possible embodiments.

I claim:

1. A bioreversibly protected phosphate compound having the formula:

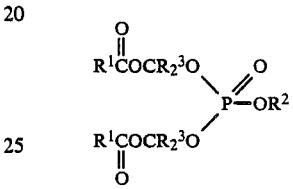

where

R¹ is selected from the group consisting of hydrogen, alkyl hydrocarbons having from 1-10 carbon atoms, aryl or alkaryl hydrocarbons having from 6-10 carbon atoms, and amines having the formula $NR^4R^5$ where $R^4$ and $R^5$ are independently hydrogen or an alkyl hydrocarbon having from 1-10 carbon atoms;

R² is nucleosid-5'-yl; and

R³ is hydrogen or methyl.

2. The compound of claim 1, wherein R¹ is selected from the group consisting of H, $CH_3$, $C_2H_5$, $C_3H_7$, $C_4H_9$, $C_6H_5$, $NH_2$, $NHCH_3$, and $N(CH_3)_2$.

3. A bioreversibly protected phosphate compound having the formula:

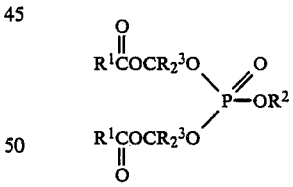

where

R¹ is selected from the group consisting of hydrogen, alkyl hydrocarbons having from 1-10 carbon atoms, aryl or alkaryl hydrocarbons having from 6-10 carbon atoms, and amines having the formula $NR^4R^5$ where $R^4$ and $R^5$ are independently hydrogen or an alkyl hydrocarbon having from 1-10 carbon atoms;

R² is 2'-deoxynucleosid-5'-yl; and

R³ is hydrogen or methyl.

4. The compound of claim 3, where R¹ is selected from the group consisting of H, $CH_3$, $C_2H_5$, $C_3H_7$, $C_4H_9$, $C_6H_5$, $NH_2$, $NHCH_3$, and $N(CH_3)_2$.

5. A bioreversibly protected phosphate compound, having the formula:

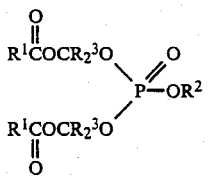

where
R¹ is selected from the group consisting of hydrogen, alkyl hydrocarbons having from 1–10 carbon atoms, aryl or alkaryl hydrocarbons having from 6–10 carbon atoms, and amines having the formula NR⁴R⁵ where R⁴ and R⁵ are independently hydrogen or an alkyl hydrocarbon having from 1–10 carbon atoms;

R² is selected from the group consisting of
2'-deoxy-5-fluorouridin-5'-yl
2'-deoxy-3'-O-acetyl-5-fluorouridin-5'-yl
2'-deoxyuridin-5'-yl
2'-deoxy-5-bromouridin-5'-yl
2'-deoxy-5-iodouridin-5'-yl
2'-deoxy-t-(bromovinyl)-uridin-5'-yl   thymidin-5'-yl, and
3'-O-acetylthymidin-5'-yl; and R³ is hydrogen or methyl.

6. The compound of claim 5, where R¹ is selected from the group consisting of H, $CH_3$, $C_2H_5$, $C_3H_7$, $C_4H_9$, $C_6H_5$, $NH_2$, $NHCH_3$, and $N(CH_3)_2$.

* * * * *

UNITED STATES PATENT AND TRADEMARK OFFICE
CERTIFICATE OF CORRECTION

PATENT NO. : 4,816,570
DATED : 3-28-89
INVENTOR(S) : David Farquhar

It is certified that error appears in the above-identified patent and that said Letters Patent is hereby corrected as shown below:

In column 3, line 53, "time" should be --type--.

In column 4, line 67, "logic" should be --ionic--.

In column 8, line 22, "partisil" should be --Partisil--.

Signed and Sealed this

Eighteenth Day of July, 1989

*Attest:*

DONALD J. QUIGG

*Attesting Officer*   *Commissioner of Patents and Trademarks*